US009232957B2

(12) United States Patent
Adams

(10) Patent No.: US 9,232,957 B2
(45) Date of Patent: Jan. 12, 2016

(54) CURVED BUR

(75) Inventor: Kenneth M. Adams, Naples, FL (US)

(73) Assignee: Athrex, Inc., Naples, FL (US)

( * ) Notice: Subject to any disclaimer, the term of this patent is extended or adjusted under 35 U.S.C. 154(b) by 3 days.

(21) Appl. No.: 13/365,888

(22) Filed: Feb. 3, 2012

(65) Prior Publication Data

US 2012/0203230 A1 Aug. 9, 2012

Related U.S. Application Data

(60) Provisional application No. 61/439,593, filed on Feb. 4, 2011.

(51) Int. Cl.
*A61B 17/00* (2006.01)
*A61B 17/32* (2006.01)

(52) U.S. Cl.
CPC ..... *A61B 17/32002* (2013.01); *A61B 17/00234* (2013.01); *A61B 2017/0023* (2013.01); *A61B 2017/00477* (2013.01); *A61B 2017/320032* (2013.01)

(58) Field of Classification Search
CPC .............. A61B 2017/320024–2017/320032; A61B 17/32002

USPC ........................................................ 606/80
See application file for complete search history.

(56) References Cited

U.S. PATENT DOCUMENTS

| | | | |
|---|---|---|---|
| 5,192,293 A * | 3/1993 | Cartwright et al. | 606/172 |
| 5,569,256 A | 10/1996 | Vaughn et al. | |
| 6,312,438 B1 * | 11/2001 | Adams | 606/159 |
| 6,656,195 B2 | 12/2003 | Peters et al. | |
| 2003/0055404 A1 | 3/2003 | Moutafis | |
| 2006/0241630 A1 | 10/2006 | Brunnett et al. | |
| 2010/0036381 A1 * | 2/2010 | Vanleeuwen et al. | 606/80 |

* cited by examiner

*Primary Examiner* — David Bates
*Assistant Examiner* — Olivia C Chang
(74) *Attorney, Agent, or Firm* — Dickstein Shapiro LLP

(57) ABSTRACT

A curved bur with an inner flexible member that is rotatably positioned within an outer tube. The curved bur has a design that constrains the flexible inner coil within the outer tube as the curved bur is rotated (without permitting the coil to stretch and to allow the bur tip to come out of the distal end of the outer tube). To ensure containment of the flexible coil within the outer tube, the outer tube is provided with a constraining neck feature at its distal end to allow the flexible inner assembly to be constrained within the outer tube, and to prevent bur extrusion. The constraining neck feature also centers the bur tip and prevents bur wobble. The curved bur may have a convex or concave bend configuration.

10 Claims, 10 Drawing Sheets

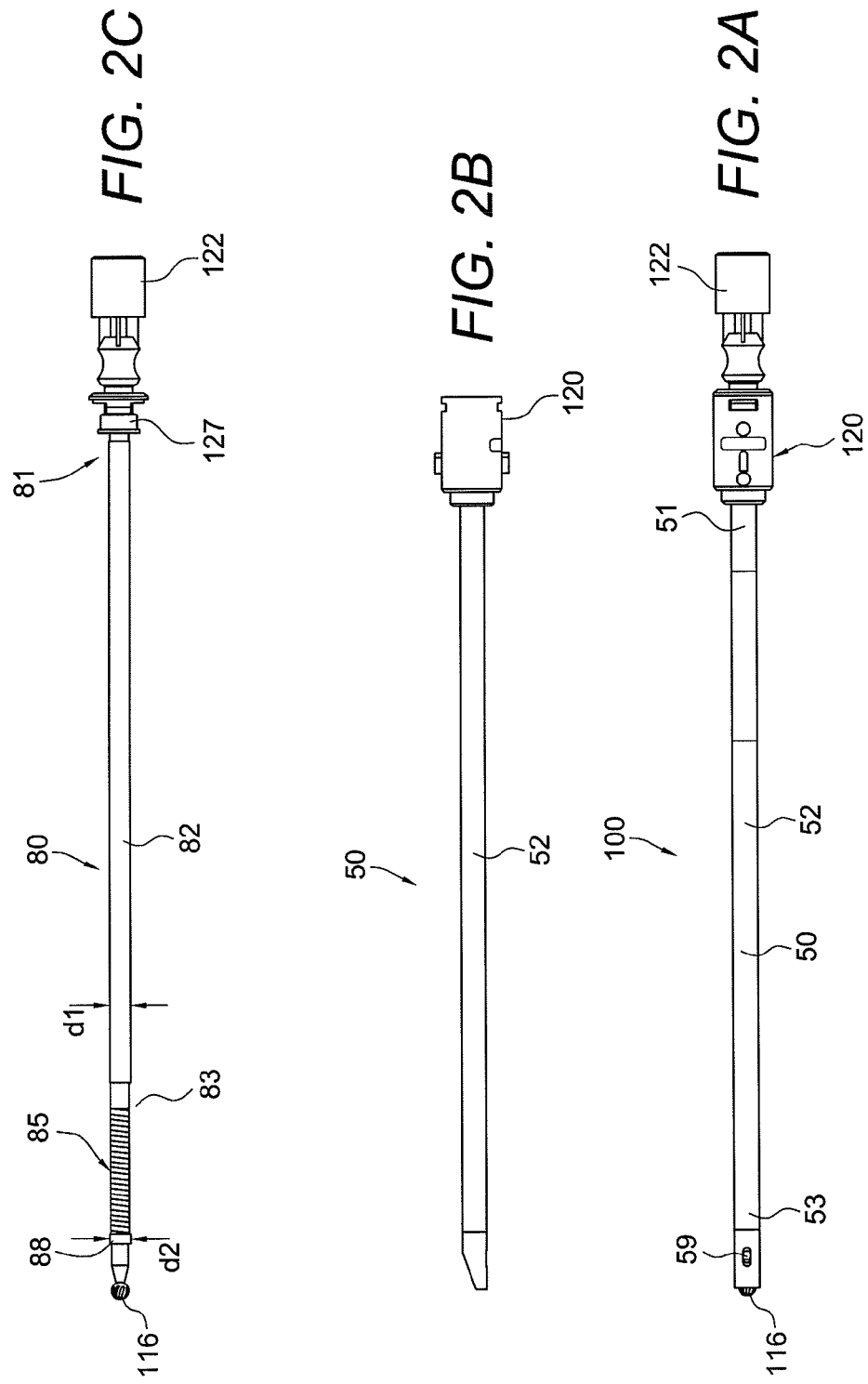

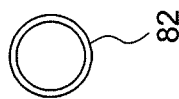
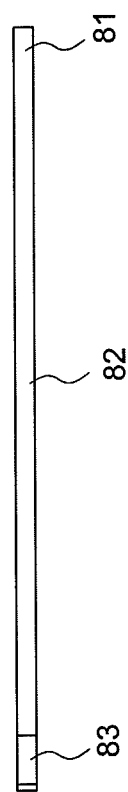

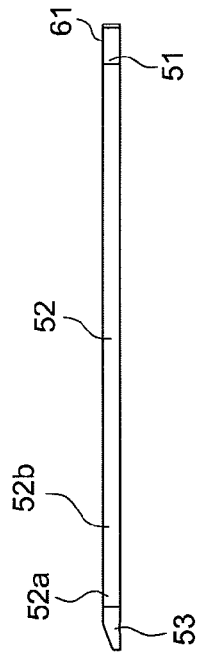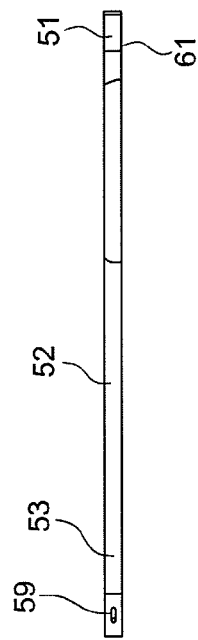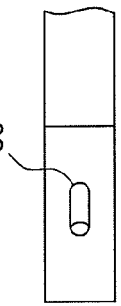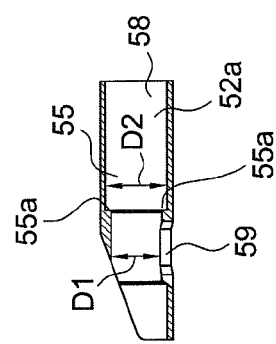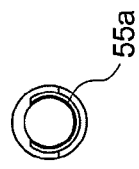

CURVED BUR

CROSS-REFERENCE TO RELATED APPLICATIONS

This application claims the benefit of U.S. Provisional Application Ser. No. 61/439,593, filed Feb. 4, 2011, the entire disclosure of which is incorporated by reference herein.

FIELD OF THE INVENTION

The present invention relates to rotary abraders used in surgery and, more particularly, to curved burs with improved designs which give the surgeon increased stability during arthroscopic procedures and improved access to the surgical site.

BACKGROUND OF THE INVENTION

Arthroscopic surgery, in which the intra-articular space is filled with fluid, allows orthopedists to efficiently perform procedures using special purpose instruments designed specifically for arthroscopy. Among these special purpose tools are various manual graspers and biters, electrosurgical devices, and powered shaver blades and rotary abraders. Shaver blades having hollow bores are typically removably coupled to a shaver handpiece and are used for cutting, resecting, boring, and abrading both soft and hard tissue at the surgical site. A rotary abrader (also known as a bur) generally includes a rotatable inner tube having an abrading head at its distal end and a fixed outer tube for rotatably receiving the inner tube. Abraders are used for abrading or shaping both soft and hard tissue as bone, cartilage or ligaments by use of the rotating abrading head.

Requirements for a rotary abrader for arthroscopy include a compact size so as to fit through small cannulae, a means for removal of debris, and a configuration which allows the surgeon to access structures within a joint, while retaining good visibility. Anatomical structures with various curvatures, such as the acetabulum in hip surgery, the talus in ankle surgery, the glenoid in shoulder surgery, and the notch in knee surgery are difficult to access with a straight bur and, if accessed, can cause excessive bending to the bur.

A surgical bur with an improved curved design that minimizes bur extrusion and increases the containment of the bur tip within the outer tube is needed. Also needed is a curved bur with a design that allows centering of the bur tip within the outer tube, while preventing bur wobble. A curved bur with a tip area that prevents extrusion of the bur from the outer hood during rotation is also needed.

SUMMARY OF THE INVENTION

The present invention provides a curved bur with an inner flexible member that is rotatably positioned within an outer tube and that consists of a spiral wrapped coil to provide torque and flexibility. The curved bur has a design that constrains the flexible inner coil within the outer tube as the curved bur is rotated (without permitting the coil to stretch and to allow the bur tip to come out of the distal end of the outer tube).

To ensure containment of the flexible coil within the outer tube, the outer tube is provided with a constraining neck feature at its distal end to allow the flexible inner assembly to be constrained within the outer tube, and to prevent bur extrusion. The constraining neck feature also centers the bur tip and prevents bur wobble. The curved bur may have a convex or concave bend configuration.

Other features and advantages of the present invention will become apparent from the following detailed description of the invention, which is provided with reference to the accompanying drawings.

BRIEF DESCRIPTION OF THE DRAWINGS

FIG. 2A illustrates a plan view of the curved bur assembly of FIG. 1A (with a rotatable flexible inner tube and an outer tube).

FIG. 2B illustrates a plan view of the outer tube of the curved bur assembly of FIG. 2A.

FIG. 2C illustrates a plan view of the rotatable flexible inner tube of the curved bur assembly of FIG. 2A.

FIGS. 3A and 3B illustrate views of the drive tube of the curved bur assembly of FIG. 2A.

FIGS. 7A-7E illustrate various views of the outer tube of the curved bur assembly of FIG. 2A.

DETAILED DESCRIPTION OF THE INVENTION

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figure 8A:
FIGS. 8A and 8B illustrate views of the flex coil of the inner assembly of the curved bur assembly of FIG. 2A.
Figure 8B:
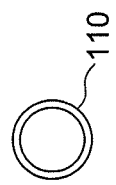
Figure 9:
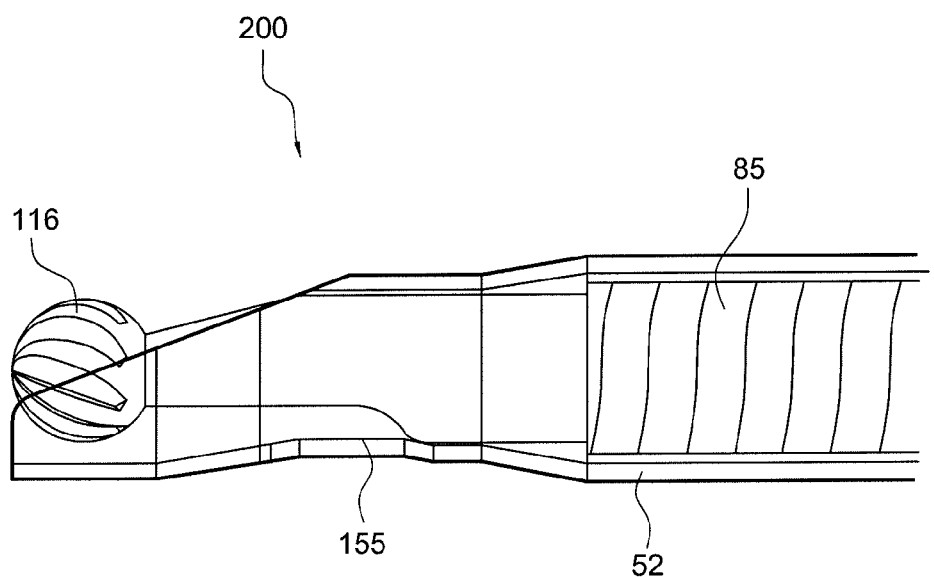
FIG. 9 illustrates a side view of a curved bur assembly according to another embodiment of the present invention (with a constraining neck region in the outer tube).

Referring now to the drawings, where like elements are designated by like reference numerals, FIGS. 1-9 illustrate various views of a rotary abrader (curved bur) 100, 100a, 100b, 200 of the present invention. FIG. 1A illustrates curved bur 100 according to a first exemplary embodiment of the present invention, i.e., with an outer tube made from two pieces and with a counterbore machined into it to accept a shoulder of the inner tip of the flexible inner assembly (when in the final assembly), to prevent the tip from extruding out of the outer hood during rotation. The shoulder acts as a stop in the tip area to prevent extrusion of the bur. FIG. 9 illustrates another exemplary curved bur 200 provided with an outer tube having a constraining neck feature at its distal end, to allow the flexible inner assembly to be constrained within the outer tube, and to prevent bur extrusion. The constraining neck feature also centers the bur tip and prevents bur wobble. FIGS. 1B and 1C illustrate two assembled curved burs 100a, 100b, one with a concave bend (FIG. 1B) and one with a convex bend (FIG. 1C).

FIGS. 2A-2C illustrate the various components of the assembled curved bur (curved rotary abrader) 100. To assemble the curved bur 100, an inner tube assembly 80 is inserted into a fixed outer tube 52 of outer assembly 50. Inner hub 122 is inserted into the outer hub 120, which may be held secure by a retaining ring. The inner hub 122 of inner tube assembly 80 includes a spring 125 (FIG. 5), a spring retainer 126 (FIG. 5), and a thrust washer 127 (FIG. 2C).

Figure 4:
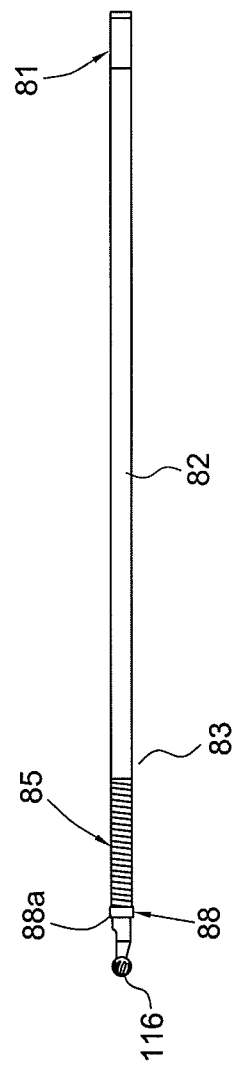
FIG. 4 illustrates a plan view of the inner flexible tube of the curved bur assembly of FIG. 2A.
Figure 5:
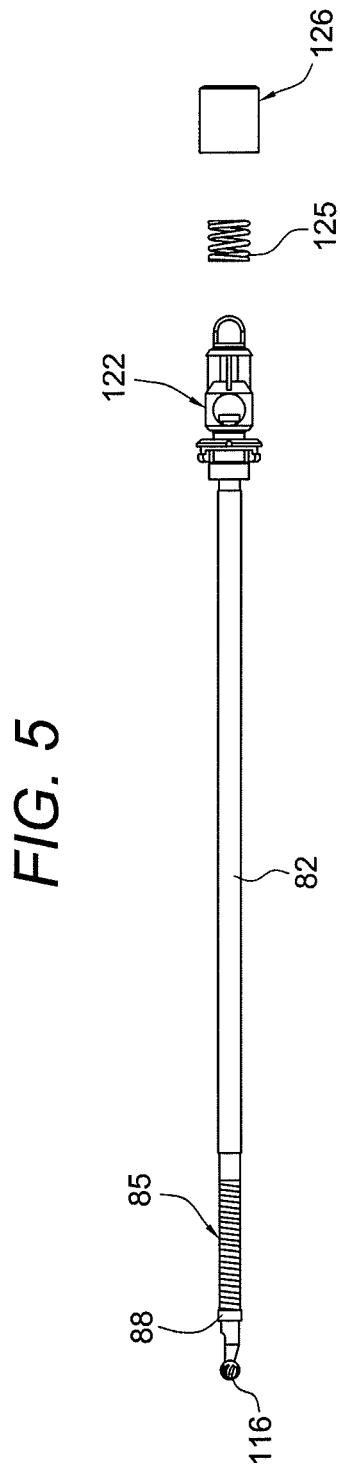
FIG. 5 illustrates the inner assembly of the curved bur assembly of FIG. 2A.

As shown in FIGS. 2C and 4, the inner tube assembly 80 has an elongated, hollow inner tubular portion 82 with a proximal end 81 and a distal end 83. Distal end 83 has affixed thereto flexible coil portion 85 terminating (at its most distal end) in a shoulder 88 machined onto it to prevent tip 116 (an abrading element or bur head or bur tip) from extruding out of the outer hood during rotation. As shown in FIG. 2C, diameter d1 of inner tube 82 (and of flexible portion 85) is smaller than the diameter d2 of the shoulder 88 by about 1 mm to about 3 mm, more preferably by about 2 mm. As detailed below, shoulder 88 of the inner tube 82 will rest on (abut) a counterbore machined into the outer hood (outer tube 52) when the inner assembly 80 is inserted into outer assembly 50 (i.e., when the rotary abrader is in the final assembly).

Figure 6A:
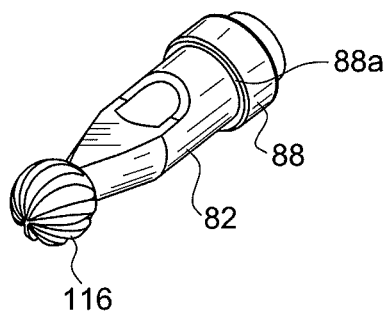
FIGS. 6A-6C illustrate various views of a bur tip of the curved bur assembly of FIG. 2A, according to a first embodiment of the present invention.
Figure 6B:
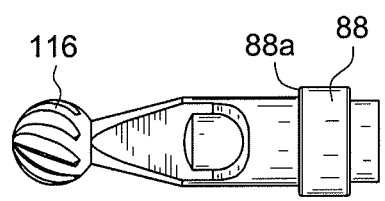
Figure 6C:
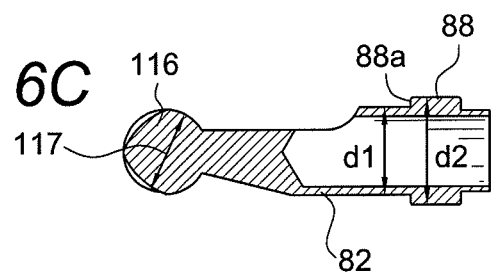
Figure 6D:
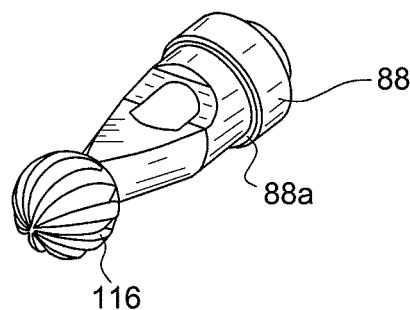
FIGS. 6D-6F illustrate various views of a bur tip of the curved bur assembly of FIG. 2A, according to a second embodiment of the present invention.
Figure 6E:
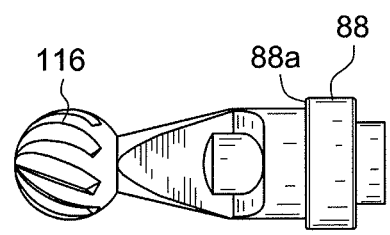
Figure 6F:
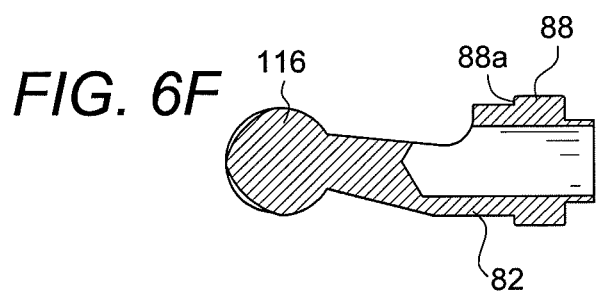

FIGS. 6A-6C and FIGS. 6D-F show enlarged views of the most distal end of rotary abrader 100, and according to two exemplary and illustrative only embodiments of the present invention. In both embodiments, the bur tip 116 of the curved bur is illustrated in the vicinity of shoulder 88. As shown in FIG. 6C, for example, diameter d2 of the shoulder 88 is larger than diameter d1 of inner tube 82.

Abrading head 116 is provided on its surface with a plurality of helical cutting flutes (for example, eight helical cutting flutes) which are arranged so that the abrading head cuts more aggressively in a forward rotational motion than in a reverse rotational motion. The abrading head may be round, as shown in FIGS. 6A-6F, or may have any other desirable size, shape or configuration, for example elongate, depending on the morphology and configuration of the tissue to be abraded. The abrading head 116 and the inner shaft 82 may be formed of stainless steel or aluminum, or of a polymer material if a disposable shaft assembly is desired.

FIGS. 8A and 8B show an enlarged view of flexible coil 85 of the inner tube assembly 80. The flexible coil inner tube 85 may comprise a tube having a hollow cylindrical configuration, the tube being sliced or cut to form a plurality of serially arranged, interconnected helical or spiral segments throughout the cylindrical wall of the tube. The helical or spiral segments are longitudinally spaced from one another lengthwise along the tube. According to another embodiment, the flexible coil 85 may be formed of a plurality of cuts provided in the tubular member, the cuts forming a series of pivoting links that are semi-circular in shape and that create an interlocked design similar to a dovetail feature. The cuts may be laser sliced or laser cut, for example, to form the semi-circular interlocked design. The plurality of pivoting semi-circular and interlocked links of the inner tube allow the surgeon to bend the tube. In an alternative embodiment, the slots may be provided in an alternating pattern (by about 180 degrees) and spaced every 0.025 inches. The slots may be laser sliced or laser cut to form a series of pivoting links that create the interlocked design.

In yet another embodiment, flexible coil inner tube 85 may be formed of two coaxial tubes, both having a hollow cylindrical configuration. Each of the two coaxial inner tubes may be sliced or cut to form a plurality of serially arranged, interconnected helical or spiral segments longitudinally spaced from one another lengthwise along each of their respective tubes. Preferably, the inner tubes are laser sliced or laser cut to form the spiral segments. In this embodiment, the spiral segments extend continuously in a helical or spiral path, i.e. an open path, along the cylindrical walls forming the tubes and about the central longitudinal axis of flexible coil inner tube 85, such that opposite ends of the helical cut do not meet. The first spiral segments may extend around the central longitudinal axis of the first inner tube in a first direction, while the second spiral segments may extend about the central longitudinal axis of the second inner tube in a second direction, which is with a clockwise or right hand turn or slant looking from distal to proximal relative to the first direction. In a preferred embodiment, the flexible coil inner tube 85 is formed of a medically acceptable material such as stainless steel.

FIGS. 7A-7E illustrate details of the fixed outer tube 52 of outer assembly 50. Outer tube 52 has a proximal end 51 and a distal end 53, and a fixed bend which is preferably made from two pieces: a first (distal) piece outer tube 52a and a second (proximal) piece outer tube 52b. Preferably, the material of the distal outer tube 52a is different from (stronger than) the material of the proximal outer tube 52b. For example, the distal portion 52a may be made from (consist essentially of) a high strength stainless steel (such as a precipitation hardening martensitic stainless steel, for example) for strength and wear resistance, whereas the proximal tubing portion 52b may be made from (consist essentially of) standard stainless steel.

Figure 1A:
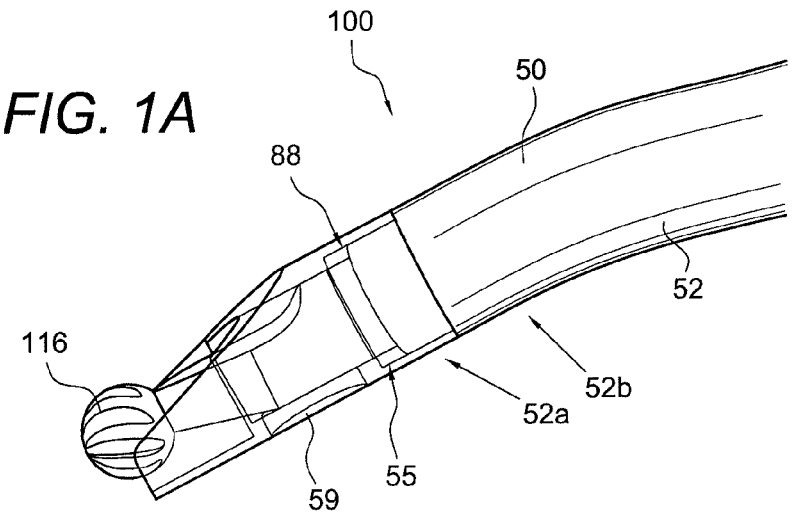
FIG. 1A is a perspective view of a curved bur according to an exemplary embodiment of the present invention (with the outer tube made from two pieces and with a counterbore machined into it to accept a shoulder of the inner tip in the final assembly).

As shown in FIG. 1A and FIG. 7D, the distal portion 52a is also provided with a counterbore 55 (corresponding to diameter D2 in FIG. 7D) which is preferably machined into it, so that the counterbore 55 will accept the shoulder 88 of the inner tip in the final assembly. The counterbore acts as a step/stop in the tip area of the abrader to prevent extrusion of the bur. As clearly shown in FIG. 7D, inner diameter D1 of the distal portion 52a is smaller than inner diameter D2 of lumen 58 of the tube 52 provided with counterbore 55. The outer diameter of the distal and proximal portions 52a, 52b is constant (except for the most distal opening for the bur 116) while the inner diameter of the distal and proximal portions 52a, 52b varies at least because of the counterbore 55 machined into the distal tubing 52a.

During assembly, a most distal surface area 55a of the counterbore 55 abuts a most distal surface area 88a (FIG. 4; FIGS. 6A-6F) of shoulder 88 of the inner assembly 80 when the inner assembly 80 is inserted into outer assembly 50. In this manner, the machined counterbore accepts the shoulder of the inner tip in the final assembly, preventing the tip from extruding out of the outer hood during rotation.

The fixed outer tube 52 may be further provided with at least one slot 59 (FIGS. 7B and 7C), for example, with a longitudinal slot disposed at its distal end and having various shapes and configurations, for example an elongated, oval configuration. The slot(s) provide a passageway located proximally from the bur tip for debris and pieces of bone or tissue produced by the abrading procedure to be drawn, by suction, from the operative site into the opening of the inner hollow shaft. A raised diamond knurl 61 (FIGS. 7A and 7B) may be also provided at the proximal end 51 of the fixed outer tube 52.

Figure 1B:
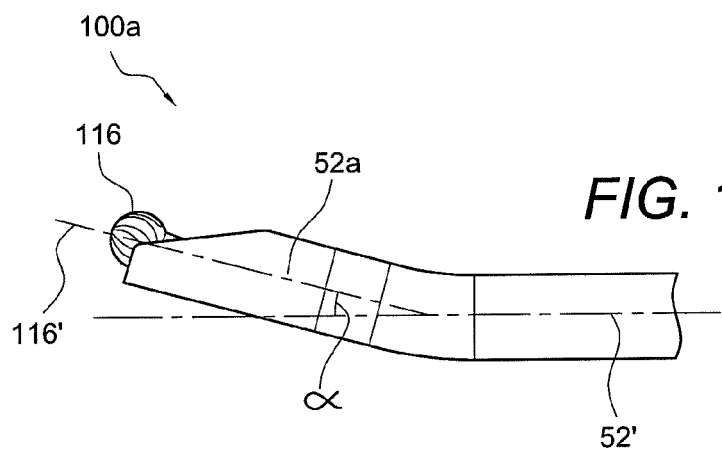
FIG. 1B is a plan view of a curved bur according to an exemplary embodiment of the present invention (with a concave bend).
Figure 1C:
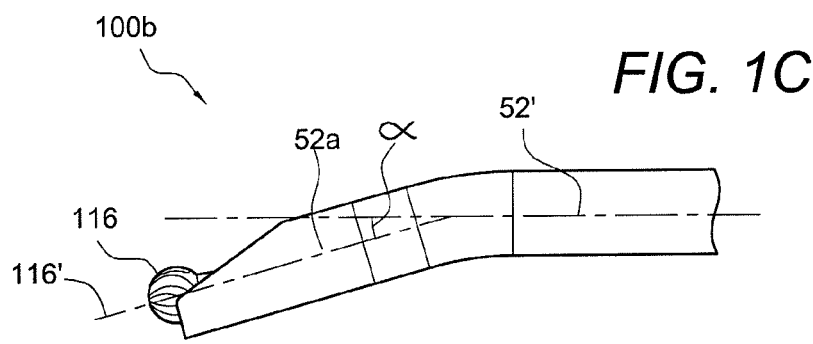
FIG. 1C is a plan view of a curved bur according to an exemplary embodiment of the present invention (with a convex bend).

As shown in FIGS. 1B and 1C, distal portion 52a of outer tube 52 forms an angle α (of about 30 to about 45 degrees, more preferably of about 30 degrees) with a central axis 52' of the outer tube 52, and extends about parallel to central axis 116' of abrading element 116.

FIG. 9 illustrates a side view of rotary abrader 200 according to another exemplary embodiment of the present invention, and provided with a reduced diameter neck portion (reduced outer diameter portion). Like in the previously-described embodiments, the reduced diameter of the neck portion 155 relative to that of the flexible coil 85 prevents extrusion of the flexible coil 85 and also centers the bur tip 116. The flexible coil 85 has a diameter larger than the diameter of the neck portion 155. The diameter of the lumen of the outer tube 52 decreases slightly and varies at slope at the distal end.

A primary drawback of prior art burs with a coil design is that the coil functions like a spring and can be stretched. With prior art bur designs, the outer tube is typically open so that, as a curved bur made with a coil design is rotated, the coil can work its way out of the distal end of the outer tube. Pulling on the device while the bur is rotating will also cause the coil to stretch. The designs of the present invention eliminate these drawbacks by providing the shoulder/counterbore features, or the constraining neck portion in the outer tube, for centering the bur tip and preventing bur wobble and extrusion.

Rotary abrader 100 of the present invention may be used for abrading or shaping both soft and hard tissue such as bone, cartilage or ligaments. For example, curved bur 100 of the present invention may be employed in an arthroscopic repair of a SLAP lesion by: (i) providing rotary cutter 100 in the proximity of the glenoid labrum; and (ii) cutting or shaping the glenoid rim with the curved bur.

Figure 10:
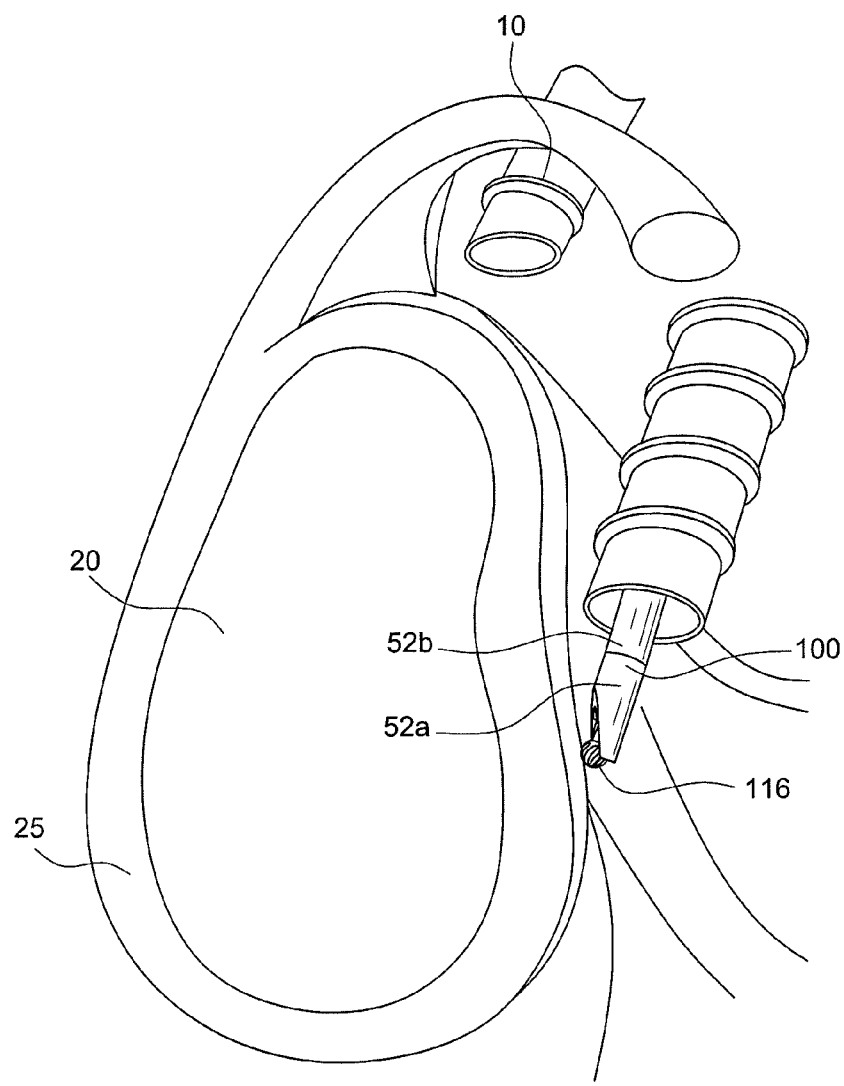
FIG. 10 is a lateral view of a human shoulder with the glenoid and labrum undergoing an exemplary method of glenoid repair with the rotary abrader of the present invention.

FIG. 10 illustrates the interior of a right human shoulder in a lateral perspective with glenoid 20 and glenoidal labrum 25 undergoing an exemplary method of glenoid repair (such as an arthroscopic repair of type II SLAP (superior labrum anterior-posterior) lesion or glenoid resurfacing) with rotary abrader 100 of the present invention. The rotary abrader 100 is introduced through cannula 10 or through an anterior portal, as shown in FIG. 10. While the glenoid adjacent to the labrum is cut/shaped, the counterbore 55 and shoulder 88 act as a step/stop in the tip area of the abrader to prevent extrusion of the bur 116.

Although the present invention has been described in relation to particular embodiments thereof, many other variations and modifications and other uses will become apparent to those skilled in the art. Therefore, the present invention is to be limited not by the specific disclosure herein, but only by the appended claims.

The invention claimed is:

1. An apparatus for abrading tissue, comprising:
   an outer assembly having an outer tube, the outer tube being made of two pieces formed of materials with different hardnesses and being provided with a distal end, a proximal end, and a fixed bend therebetween, wherein the distal end of the outer tube is provided with a counterbore monolithically formed into an inner lumen of the outer tube;
   an inner assembly rotatably positioned within the outer tube, wherein an inner tube of the inner assembly is removable from the outer tube of the outer assembly, the inner tube having a proximal end and a distal end; and
   an abrading element located at a most distal end of the inner tube,
   wherein the distal end of the inner tube has affixed thereto a flexible coil portion proximal to the abrading element, the flexible coil portion terminating in a shoulder at its most distal end, the shoulder being machined onto the inner tube and having a width greater than a width of the inner lumen of the distal end of the outer tube, and wherein the shoulder of the inner tube rests on the counterbore of the outer tube when the inner assembly is inserted into the outer tube to center the abrading element and prevent wobble and extrusion of the abrading element out of the outer tube during rotation, and without permitting the flexible coil portion to stretch.

2. The apparatus of claim 1, wherein the fixed bend of the outer tube is formed of a first region of a first material and of a second region of a second material, wherein the first material is different from the second material.

3. The apparatus of claim 2, wherein the first material is a precipitation hardening martensitic stainless steel, and the second material is standard stainless steel.

4. The apparatus of claim 1, wherein the fixed bend forms an angle with a central axis of the proximal end of the outer tube.

5. The apparatus of claim 4, wherein the angle is of about 30 degrees.

6. The apparatus of claim 1, wherein the distal end of the outer tube forms an angle of about 0 degrees with a central axis of the abrading element when the inner assembly is rotatably positioned within the outer tube.

7. The apparatus of claim 1, wherein the distal end of the outer tube extends about parallel to the central axis of the abrading element and surrounds at least a portion of the abrading element when the inner assembly is rotatably positioned within the outer tube.

8. The apparatus of claim 1, further comprising at least one aspiration port located near the distal end of the outer tube.

9. A curved instrument for removing tissue, comprising:
   an inner assembly rotatably positioned within an outer assembly, wherein an inner tube of the inner assembly is removable from an outer tube of the outer assembly, and wherein a distal end of the inner tube has affixed thereto a flexible coil terminating distally in a shoulder machined onto the inner tube,
   a hub formed at a proximal end of each of the inner assembly and the outer assembly;
   an abrading element located at a most distal end of the inner tube of the inner assembly;
   a hood located at a distal end of the outer tube of the outer assembly, wherein the hood is formed integrally with the outer tube and of a material different from a material of the outer tube, and wherein the hood forms an angle of about 30 degrees with a central axis of the outer tube, and an angle of about 0 degrees with a central axis of the abrading element when the inner assembly is rotatably positioned within the outer assembly,
   wherein the shoulder of the inner tube abuts, at its distal end, a counterbore formed monolithically into an inner lumen of the hood to center the abrading element and prevent wobble and extrusion of the abrading element out of the outer tube during rotation, and
   wherein the shoulder has a diameter greater than an outer diameter of the inner tube but smaller than an inner diameter of the hood.

10. The curved instrument of claim 9, wherein the material of the hood is harder than the material of the outer tube.

* * * * *